United States Patent [19]

Ushakoff

[11] 4,127,134

[45] Nov. 28, 1978

[54] GAS-ABSORBING PACER AND METHOD OF FABRICATION

[75] Inventor: Alexis E. Ushakoff, Plantation, Fla.

[73] Assignee: Cordis Corporation, Miami, Fla.

[21] Appl. No.: 786,112

[22] Filed: Apr. 11, 1977

[51] Int. Cl.² ............................................. A61N 1/36
[52] U.S. Cl. .................................. 128/419 P; 429/57
[58] Field of Search ...................... 128/419 P, 419 PS; 252/181.1; 316/25; 429/57, 59

[56] References Cited

U.S. PATENT DOCUMENTS

| | | | |
|---|---|---|---|
| 3,287,174 | 11/1966 | Hennigen et al. | 429/57 X |
| 3,749,101 | 7/1973 | Williamson | 128/419 P |
| 3,926,198 | 12/1975 | Kolenik | 128/419 P |
| 3,943,937 | 3/1976 | King et al. | 128/419 P |

*Primary Examiner*—William E. Kamm

*Attorney, Agent, or Firm*—Kenway & Jenney

[57] ABSTRACT

The cardiac pacer disclosed herein is of the type in which pulse-generating circuitry is energized by an electro-chemical cell of a type which gives off hydrogen during depletion of the cell, e.g. a mercury battery. A hermetically sealed case is provided for enclosing both the circuitry and the electro-chemical cell to protect them from body fluids, the case having at least one feed-through terminal for coupling pulses generated by the circuitry to a lead adapted for contacting a patient's heart. A getter is disposed within the case consisting essentially of a solid mass of palladium metal having a thin layer of palladium oxide formed on the outer surface thereof. A preferred method of forming the palladium oxide is by anodizing the mass of palladium metal in a sulphuric acid bath.

7 Claims, 3 Drawing Figures

GAS-ABSORBING PACER AND METHOD OF FABRICATION

BACKGROUND OF THE INVENTION

The present invention relates to implantable cardiac pacers and more particularly to such a pacer which is hermetically sealed.

While pacers of a construction in which both pulse-generating circuitry and batteries are encased in plastic resin such as epoxy have been used successfully for many years, a continuing concern has been the effect moisture from the patient's body may have on circuit components if it penetrates the enclosure over time. Accordingly, attempts have been made from time to time to construct a hermetically sealed pacer, that is, a pacer in which the pulse-generating circuitry and the batteries powering the circuitry are contained within a metallic case which is sealed so as to be effectively impervious with respect to either gases or liquids. Signals into and out of the circuitry are coupled through the case by means of feed-through terminals of various types known in the art, e.g. those employing glass-to-metal seals and the like.

A persistent problem in arriving at a satisfactory hermetically sealed pacer construction has been the management of the atmosphere within the hermetically sealed case. While the electronic components employed for generating pulses may typically be considered to be essentially inert, the batteries are not. The most prevalent type of battery for powering cardiac pacemakers, i.e. due to its relatively long life and stability, is that employing so-called mercury cells. The electro-chemical reaction taking place in these cells generates hydrogen. The cells themselves are typically constructed so as to vent this hydrogen in a predetermined and controllable manner. In pacers constructed with a resin encasement or encapsulation, the hydrogen can permeate the casing material and is thus given off by the pacer and eventually absorbed by the fluids in the patient's body. The rate of discharge of hydrogen is sufficiently low that dangerously high pressures are not encountered. In a hermetically sealed pacer, however, the internal pressure inside the hermetically sealed case can continue to grow until it may reach levels which will bulge the case, changing its buoyancy, and possibly damage electronic components. The present invention involves the management of the atmosphere within a hermetically sealed cardiac pacer in such a manner that dangerous pressures are avoided.

Among the several objects of the present invention may be noted the provision of a novel, hermetically sealed implantable cardiac pacer and method of fabrication; the provision of such a pacer which is energizable by mercury batteries; the provision of such a pacer which is highly reliable; the provision of such a pacer in which electronic components are not subjected to abnormally high temperatures; and the provision of such a pacer which is of relatively simple and inexpensive construction. Other objects and features will be in part apparent and in part pointed out hereinafter.

SUMMARY OF THE INVENTION

An implantable cardiac pacer according to the present invention employs circuitry which, when energized, operates to controllably generate electrical pulses suitable for cardiac stimulation and electro-chemical cells for energizing that circuitry, the cells being of a type which give off hydrogen during depletion. The circuitry and the cells are enclosed in a metal case for protecting them from body fluids, the case being hermetically sealed and having at least one feed-through terminal for coupling pulses generated by the circuitry to a lead adapted for contacting a patient's heart. Included within the case is a getter for hydrogen consisting essentially of a solid mass of palladium metal having a thin layer of palladium oxide formed on the outer surface thereof. In the preferred method of fabricating this pacer, the palladium oxide is formed on the outer surface of the palladium metal mass by anodizing the palladium in a sulphuric acid bath.

BRIEF DESCRIPTION OF THE DRAWINGS

Corresponding reference characters indicate corresponding parts throughout the several views of the drawings.

DESCRIPTION OF THE PREFERRED EMBODIMENT

Figure 1:
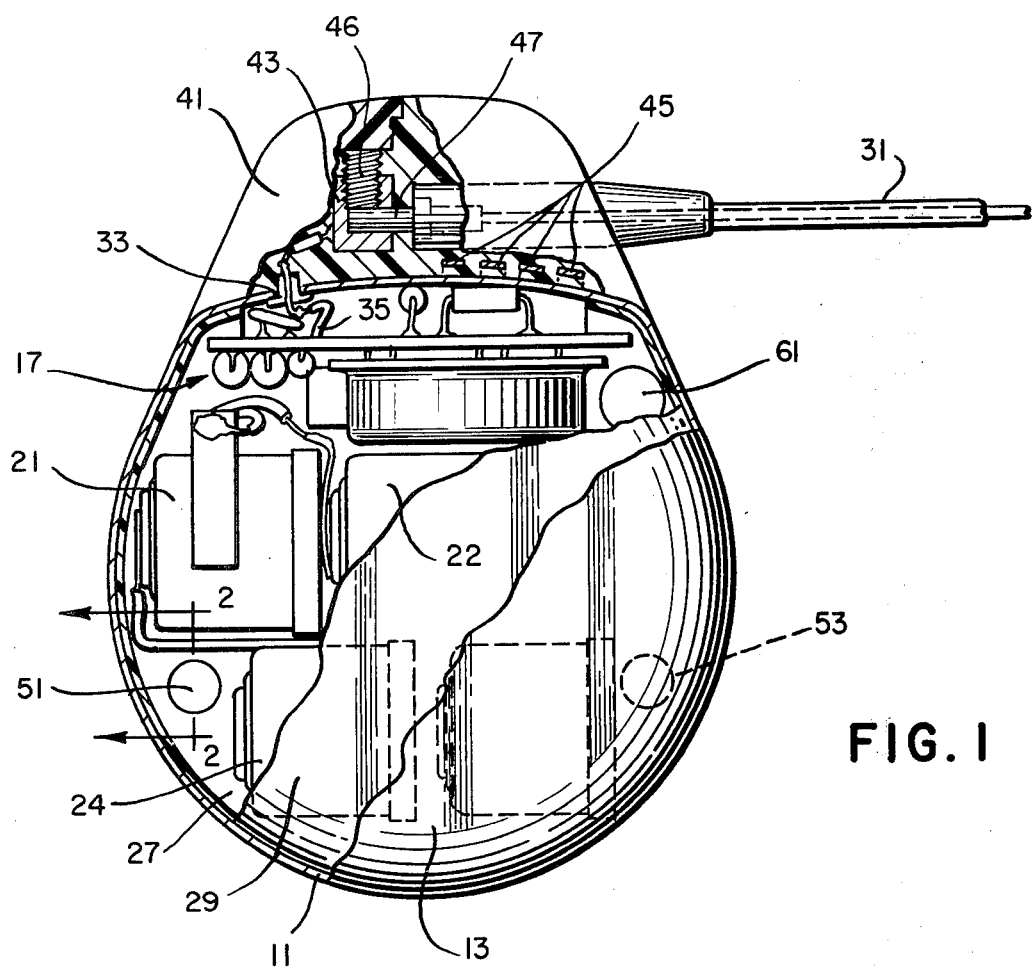
FIG. 1 is a side view, with parts broken away, of an implantable cardiac pacer constructed in accordance with the present invention.

Referring now to FIG. 1, the cardiac pacer illustrated there is of a type which may be described as being hermetically sealed, that is, the internal workings of the pacer are enclosed in a case which is essentially impervious to either liquids or gases. The case is fabricated in two halves 11 and 13 which are subsequently joined by TIG welding to form a sealed vessel. The top half 13 of the casing is shown broken away in FIG. 1 to reveal the contents of the case.

Within the casing is the pacer's circuitry, indicated generally at 17, and a battery of five mercury cells 21–25. The electro-chemical cells 21–25 are of a type which give off hydrogen during depletion of the cells, e.g. the mercury batteries typically used for powering cardiac pacemakers. To properly locate these components within the casing, they are nested within a polyethylene retainer assembly comprising lower and upper parts 27 and 29. The top part 29 is shown broken away in the drawing to facilitate the illustration. If desired, the circuitry and batteries may also be potted within the retainer shells 27 and 29 using a suitable casting or potting compound such as a silicone rubber.

The circuitry shown by way of illustration is of a type adapted for use with a unipolar lead arrangement, i.e. a lead comprising a single conductor as indicated at 31. With such an arrangement, the distal end of the lead 31 is placed in contact with the heart and a reference potential is established through a metallic surface at the pacer itself, i.e. the pacer case. This arrangement is described in greater detail in the Murphy et al. U.S. Pat. No. 3,253,595 entitled Cardiac Pacer Electrode System. As is understood by those skilled in the art, the single lead may be used for both sensing and stimulation and various types of pacing modes may be provided.

For connecting the circuitry to the lead 31, a feed-through terminal 33 is provided in the lower case half 11. The feed-through terminal is of a type, e.g. one employing metal/glass seals, which preserves the hermeticity of the case. When the circuitry and battery are placed in the case, connections are provided between the circuitry and the feed-through terminal, e.g. by means of a lead 35, and also between the circuitry and the case, e.g. by means of a lead welded to the case (not shown).

After the circuitry and batteries have been connected to the feed-through terminal and the casing, the covering half 13 of the metal case is welded into place to complete the hermetically sealed vessel. A plastic cap assembly 41 with a lead connector 43 is cast over the feed-through terminal. Preferably, a plurality of tabs 45 are welded to at least one of the case halves so as to facilitate a secure mechanical attachment of the cap assembly as it is cast in place. The connector 43 comprises a set screw clamp 46 for securing and obtaining a reliable electrical contact to the terminal sleeve 47 conventionally extending from the proximal end of the lead 31.

As is understood by those skilled in the art, the mercury batteries commonly employed to power pacemakers are arranged so that they periodically vent hydrogen gas. This venting prevents a buildup of pressure within the cases of the batteries themselves. The volume of the typical pacer case, however, is not sufficient to accept the released gas without building up unacceptably high pressures, e.g. pressures which might damage the electronic components employed in the circuitry 15 or bulge or distort the case, perhaps causing cracks in the welds which could lead to corrosion and ultimate failure. In accordance with the present invention, the pacer employs a pair of novel hydrogen getters 51 and 53 which absorb the hydrogen given off by the cells so as to maintain acceptable pressures within the sealed case.

Figure 2:
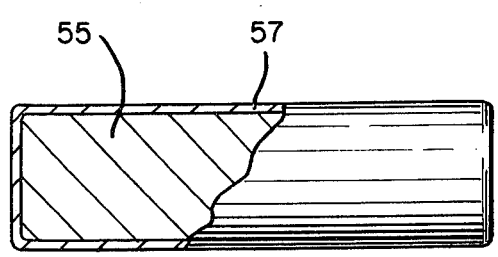
FIG. 2 is a sectional view to enlarged scale, taken substantially on the line 2—2 of FIG. 1, of a hydrogen getter employed in the pacer of FIG. 1.

As illustrated in FIG. 2, each of the getters 51 and 53 consists essentially of a solid mass of palladium metal 55 having a thin layer of palladium oxide 57 formed on the outer surface thereof. While it has previously been proposed to employ palladium oxide as a getter for hydrogen (see for example U.S. Pat. No. 3,287,174), the use of palladium oxide itself has not been deemed acceptable in the cardiac pacer environment since the gettering process results in the production of water as the palladium oxide is reduced to palladium during its combination with hydrogen. The presence of substantial water vapor within the sealed casing may induce corrosion and degradation of the circuit components and otherwise adversely affect the operation of the pacer.

It has been determined that solid metallic palladium is capable of absorbing and holding substantial amounts of hydrogen but it was likewise found the rate of absorption is very slow and may be subject to subtle surface effects, e.g. the absence of absolute surface cleanliness or the presence of surface films, which would be difficult to control and/or detect. While the rate of absorption problem can be somewhat ameliorated by utilizing finely divided palladium, i.e. palladium black, such material is extremely difficult to handle and package in any form which would make it useful as a getter in the cardiac pacer environment. Further, the total gettering capacity for unit volume of palladium black is less than that of solid metallic palladium in that the total mass of palladium metal for a given volume is significantly less.

In accordance with one aspect of the present invention, the rate of absorption of hydrogen into a mass of essentially solid metallic palladium is greatly increased by anodizing the palladium so as to form a layer of palladium oxide on the outer surface thereof. In a presently preferred method of fabricating the getters, palladium metal rod 0.190 inches in diameter is anodized for three minutes against a carbon or platinum cathode in ten percent sulphuric acid in distilled water, using a current density of one ampere per inch of rod length. After anodizing, the palladium rods are washed in distilled water and dried. After cutting to the desired length, e.g. 0.50 inches in the embodiment illustrated, the finished getters are sealed in air in plastic bags until they are ready to be incorporated into completed pacers. The weight of each getter thus constructed is about 2.9 grams and the getters so constructed have gettering ability equal to approximately 60 liters torr hydrogen per gram of palladium metal. In another embodiment, where greater getter capacity was desired, a third length of anodized palladium rod, 0.170 inches diameter by 1.20 inches long, was nested against and parallel to the rows of cylindrical battery cells.

If desired, e.g. in connection with testing for gettering capacity, the getters can be regenerated by heating. For example, a hydrogen-saturated palladium getter constructed in accordance with the present invention can be essentially completely regenerated in 12 minutes when exposed to a furnace temperature of 450° C.

Figure 3:
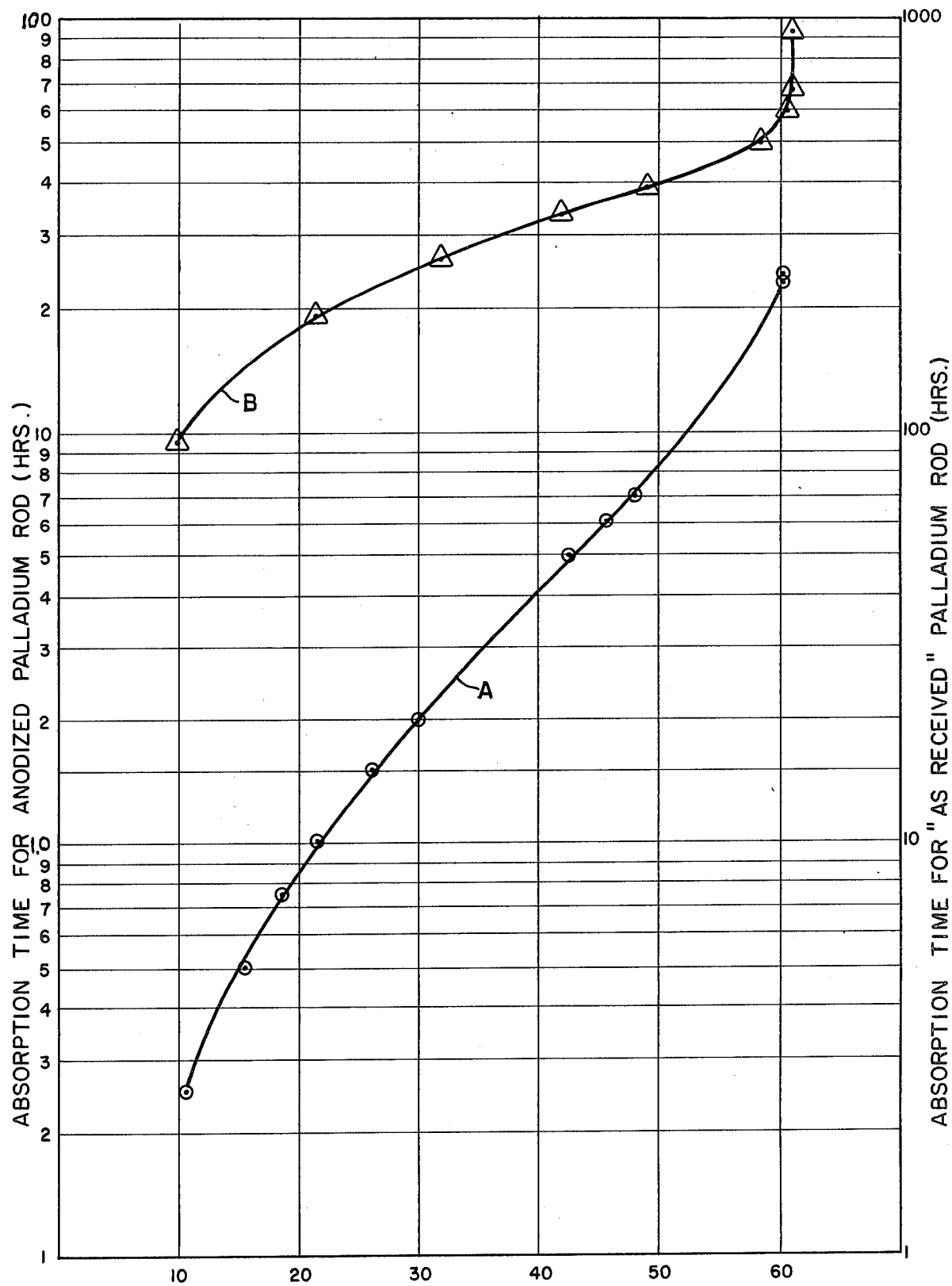
FIG. 3 is a graph representing the hydrogen-getting performance of anodized palladium as compared with solid palladium, un-anodized.

As indicated previously, an important aspect of the present invention is that the anodizing greatly increases the rate at which the palladium getter will absorb hydrogen. With getters of the size described, the time required to essentially saturate the palladium with hydrogen is reduced from over 650 hours to 23 hours by the anodizing. FIG. 3 is a graph representing the absorption time versus quantity of hydrogen absorbed for both an anodized getter, curve A, and the original or un-anodized palladium rod segment, curve B. It should be noted that the absorption time is plotted on a logarithmic scale and that different scales are used on the two samples. It thus will be appreciated that the actual rate change is much more than an order of magnitude.

While the improvement in rate of absorption is important to assure that excess pressures cannot develop within the pacer case, an almost equally important consideration is the resultant ability to be able to test the getters to establish that both the rate of absorption and absorption capacity are sufficient for the intended purpose. As will be understood, cardiac pacers must be constructed as exceptionally high reliability devices and assurance is needed that each component will perform as predicted. Accordingly, the getters must be empirically tested, e.g. on a sample or percentage basis. If un-anodized getters were utilized, the testing procedure would be inordinately long and significant quantities of getters would have to be tied up awaiting the results of the related testing procedures, i.e. before being installed in pacers.

While the palladium oxide coating on each getter 51 and 53 itself absorbs some hydrogen and produces some water, the effect is apparently self-limiting and essentially negligible. The slight water film developed does not impair the migration of hydrogen to the underlying palladium metal and does not apparently create a sufficient partial pressure of water vapor within the pacer case to cause any problems with the electronic components employed in the circuitry 15. However, as a precautionary measure, a moisture-absorbent desiccant pellet is preferably included within the pacer case, adjacent the circuitry as indicated at 61 in FIG. 1. This desiccant pellet can also absorb any water vapor directly given off by the electro-chemical cells 21–25. A presently preferred form of a desiccant is that available from Multiform Desiccant Products, Inc. under the trade name NATRASORB ®4-A, formed into pellets in accordance with the manufacturer's data sheets on the product.

In view of the foregoing, it may be seen that several objects of the present invention are achieved and other advantageous results have been attained.

As various changes could be made in the above constructions without departing from the scope of the invention, it should be understood that all matter contained in the above description or shown in the accompanying drawings shall be interpreted as illustrative and not in a limiting sense.

What is claimed is:

1. An implantable cardiac pacer comprising:
   circuitry which, when energized, operates to controllably generate electrical pulses suitable for cardiac stimulation;
   means for energizing said circuitry, including at least one electro-chemical cell of a type which gives off hydrogen during depletion of the cell;
   a case enclosing said circuitry and said cell for protecting them from body fluids, said case being hermetically sealed and having at least one feed-through terminal for coupling pulses generated by said circuitry to a lead adapted for contacting a patient's heart;
   also within said case, a getter comprising a solid mass of palladium metal for absorbing hydrogen given off by the cell, said solid mass having a thin layer of palladium oxide formed on the outer surface thereof for greatly increasing the rate of absorption of hydrogen into the mass of palladium metal.

2. A pacer as set forth in claim 1 including a pair of cylindrical getters each of which is about 0.50 inches long and about 0.19 inches in diameter.

3. A pacer as set forth in claim 1 wherein said layer is formed on said mass of palladium metal by anodizing in sulphuric acid.

4. A pacer as set forth in claim 1 wherein said energizing means includes a mercury battery comprising a plurality of cells.

5. A method of fabricating a cardiac pacer which comprises:
   providing a suitably shaped solid mass of palladium metal;
   anodizing said metallic mass to form on the outer surface thereof a thin layer of palladium oxide;
   hermetically sealing within a case:
     the anodized mass of palladium metal;
     circuitry which, when energized, operates to generate electrical pulses suitable for cardiac stimulation; and
     means for energizing said circuitry, including at least one electro-chemical cell of a type which gives off hydrogen during depletion of the cell;
   said case having a feed-through terminal for coupling pulses generated by said circuitry to a lead adapted for contacting a patient's heart.

6. The method as set forth in claim 5 wherein the anodization of said palladium metal is performed in diluted sulphuric acid.

7. The method as set forth in claim 5 wherein said energizing means includes a plurality of mercury cells sealed in said case.